US00PP18944P2

(12) United States Plant Patent
Smith

(10) Patent No.: US PP18,944 P2
(45) Date of Patent: Jun. 17, 2008

(54) ***HIBISCUS* PLANT NAMED 'CHERRY BRANDY'**

(50) Latin Name: ***Hibiscus* hybrid**
Varietal Denomination: Cherry Brandy

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,531

(22) Filed: Dec. 18, 2006

(51) Int. Cl.
*A01H 5/00* (2006.01)

(52) U.S. Cl. ..... Plt./257

(58) Field of Classification Search ..... Plt./257
See application file for complete search history.

(56) References Cited

PUBLICATIONS

UPOV ROM GTITM Computer Database, GTI Jouve Retrieval Software 2007/02 Citation for 'Cherry Brandy'.*

* cited by examiner

*Primary Examiner*—Wendy C. Haas
(74) *Attorney, Agent, or Firm*—C. A. Whealy

(57) ABSTRACT

A new and distinct cultivar of Hardy *Hibiscus* plant named 'Cherry Brandy', characterized by its upright and outwardly spreading plant habit; green and purple-colored leaves that are palmately lobed; early flowering habit; and large single dark red-colored flowers.

1 Drawing Sheet

Botanical designation: *Hibiscus* hybrid.
Cultivar denomination: 'Cherry Brandy'.

BACKGROUND OF THE INVENTION

The present invention relates to a new and distinct cultivar of *Hibiscus,* botanically known as *Hibiscus* hybrid, commercially referred to as Hardy *Hibiscus* and hereinafter referred to by the name 'Cherry Brandy'.

The new *Hibiscus* is a product of a planned breeding program conducted by the Inventor in Alva, Fla. The objective of the breeding program is to create new freely-branching Hardy *Hibiscus* cultivars with a compact plant habit and desirable flower color.

The new Hardy *Hibiscus* originated from a cross-pollination made by the Inventor in Alva, Fla. during the spring of 2002, of the *Hibiscus* hybrid cultivar Peppermint Schnapps, disclosed in U.S. Plant patent application Ser. No. 11/641,533, as the female, or seed, parent with the *Hibiscus* hybrid cultivar Kopper King, disclosed in U.S. Plant Pat. No. 10,793, as the male, or pollen, parent. The cultivar Cherry Brandy was discovered and selected by the Inventors as a flowering plant within the progeny of the stated cross-pollination in a controlled environment in Alva, Fla. on May 20, 2003.

Asexual reproduction of the new Hardy *Hibiscus* by vegetative terminal cuttings in a controlled environment in Alva, Fla. since June, 2003, has shown that the unique features of this new Hardy *Hibiscus* are stable and reproduced true to type in successive generations.

SUMMARY OF THE INVENTION

The cultivar Cherry Brandy has not been observed under all possible environmental conditions. The phenotype may vary somewhat with variations in environment and cultural practices such as temperature an light intensity without, however, any variance in genotype.

The following traits have been repeatedly observed and are determined to be the unique characteristics of 'Cherry Brandy'. These characteristics in combination distinguish 'Cherry Brandy' as a new and distinct cultivar of Hardy *Hibiscus:*

1. Upright and outwardly spreading plant habit.
2. Green and purple-colored leaves that are palmately lobed.
3. Early flowering habit.
4. Large single dark red-colored flowers.

Plants of the new Hardy *Hibiscus* can be compared to plants of the female plant, the cultivar Peppermint Schnapps. In side-by-side comparisons conducted in Alva, Fla., plants of the new Hardy *Hibiscus* differed from plants of the cultivar Peppermint Schnapps in the following characteristics:

1. Plants of the new Hardy *Hibiscus* were denser than plants of the cultivar Peppermint Schnapps.
2. Plants of the new Hardy *Hibiscus* and the cultivar Peppermint Schnapps differed in leaf form and color.
3. Plants of the new Hardy *Hibiscus* flowered later than plants of the cultivar Peppermint Schnapps.
4. Flowers of plants of the new Hardy *Hibiscus* and the cultivar Peppermint Schnapps differed in flower color.

Plants of the new Hardy *Hibiscus* can be compared to plants of the male parent, the cultivar Kopper King. In side-by-side comparisons conducted in Alva, Fla., plants of the new Hardy *Hibiscus* differed from plants of the cultivar Kopper King in the following characteristics:

1. Plants of the new Hardy *Hibiscus* were more freely branching and denser than plants of the cultivar Kopper King.
2. Plants of the new Hardy *Hibiscus* and the cultivar Kopper King differed in leaf color.
3. Plants of the new Hardy *Hibiscus* flowered later than plants of the cultivar Kopper King.

4. Plants of the new Hardy *Hibiscus* had smaller flowers than plants of the cultivar Kopper King.
5. Plants of the new Hardy *Hibiscus* and the cultivar Kopper King differed in flower color.

Plants of the new Hardy *Hibiscus* can be compared to plants of the *Hibiscus* hybrid cultivar Fireball, disclosed in U.S. Plant Pat. No. 13,631. In side-by-side comparisons conducted in Alva, Fla., plants of the new Hardy *Hibiscus* differed from plants of the cultivar Fireball in the following characteristics:

1. Plants of the new Hardy *Hibiscus* were taller than plants of the cultivar Fireball.
2. Plants of the new Hardy *Hibiscus* were more freely branching and denser than plants of the cultivar Fireball.
3. Plants of the new Hardy *Hibiscus* and the cultivar Fireball differed in leaf color.
4. Plants of the new Hardy *Hibiscus* flowered later than plants of the cultivar Fireball.

BRIEF DESCRIPTION OF THE PHOTOGRAPHS

The accompanying colored photographs illustrate the overall appearance of the new Hardy *Hibiscus,* showing the colors as true as it is reasonably possible to obtain in colored reproductions of this type. Colors in the photographs may differ slightly from the color values cited in the detailed botanical description which accurately describe the colors of the new Hardy *Hibiscus.*

The photograph at the bottom of the sheet comprises a side perspective view of a typical flowering plant of 'Cherry Brandy' grown in a container.

The photograph at the top of the sheet comprises a close-up view of a typical flower of 'Cherry Brandy'.

DETAILED BOTANICAL DESCRIPTION

The aforementioned photographs and following observations, measurements and values describe plants grown during the summer in Alva, Fla. in 1.5-gallon containers in a polypropylene-covered shadehouse and under conditions which closely approximate commercial Hardy *Hibiscus* production. During the production of the plants, day temperatures ranged from about 29° C. to about 35° C. and night temperatures ranged from about 21° C. to about 24° C. Plants were pinched one time and were about two months old when the photographs and the description were taken. In the description, color references are made to The Royal Horticultural Society Color Chart, 1995 Edition, except where general terms of ordinary dictionary significance are used.

Botanical classification: *Hibiscus* hybrid cultivar Cherry Brandy.

Parentage:

*Female, or seed, parent.*—*Hibiscus* hybrid cultivar Peppermint Schnapps, disclosed in U.S. Plant patent application Ser. No. 11/641,533.

*Male or pollen parent.*—*Hibiscus* hybrid cultivar Kopper King, disclosed in U.S. Plant Pat. No. 10,793.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick becoming fibrous and enlarged; white in color.

*Rooting habit.*—Freely branching.

Plant description:

*Plant form and growth habit.*—Upright and outwardly spreading plant habit. Vigorous growth habit.

*Branching habit.*—Freely branching, usually about four lateral branches develop after pinching.

*Plant height.*—About 45 cm.

*Plant diameter* (*area of spread*).—About 48 cm.

Lateral branch description:

*Length.*—About 33 cm.

*Diameter.*—About 1.5 cm.

*Internode length.*—About 2.3 cm.

*Strength.*—Strong.

*Texture.*—Smooth, glabrous.

*Color.*—182A to 182B.

Foliage description:

*Arrangement.*—Alternate, single.

*Length.*—About 18 cm.

*Width.*—About 14 cm.

*Shape.*—Palmately lobed, mapleleaf-shaped.

*Apex.*—Acuminate; reflexing.

*Base.*—Cordate.

*Margin.*—Shallowly crenate.

*Texture, upper and lower surfaces.*—Smooth, glabrous.

*Venation pattern.*—Palmate.

*Color.*—Developing foliage, upper surface: 139A. Developing foliage, lower surface: 147B. Mature foliage, upper surface: 139A tinted with 184B; venation, 185A. Leaf color becoming more bronzed with development. Mature foliage, lower surface: 147B; venation, 177B.

*Petiole.*—Length: About 9.2 cm. Diameter: About 4.5 mm. Texture, upper and lower surfaces: Smooth, glabrous. Color, upper surface: 187B. Color, lower surface: 146A tinted with 183B.

Flower description:

*Flower arrangement.*—Flowers arranged singly originating from leaf axils. Lateral stems with typically one open flower and about three to four flower buds. Flowers face mostly outwardly.

*Flower appearance.*—Large, round dark red-colored flowers. Flowers last for about one or two days. Flowers persistent. Flowers not fragrant.

*Natural flowering season.*—Usually spring and summer or during periods of warm weather. Early flowering habit, plants begin flowering about eleven weeks after pinching.

*Flower diameter.*—About 10.5 cm.

*Flower length* (*height*).—About 7 cm.

*Flower bud.*—Length: About 6 cm. Diameter: About 2.6 cm. Shape: Ovate. Color: 53B.

*Petals.*—Arrangement: Corolla consists of five petals that are fused at base; petals imbricate. Length: About 9.5 cm. Width: About 10.8 cm. Shape: Obovate to fan-shaped to slightly reniform. Apex: Rounded. Base: Acute to attenuate. Margin: Entire; slightly sinuate. Texture: Upper surface: Smooth, glabrous; slightly ridge. Lower surface: Smooth, glabrous; veins prominent. Color: When opening, upper surface: 59B to 59C. When opening, lower surface: 60B. Fully opened, upper surface: 59B; towards the base, 53A; venation, 59B. Fully opened, lower surface: 60A; venation, 53B.

*Sepals.*—Appearance: Five sepals fused at the base into a star-shaped calyx. Length: About 2.8 cm. Width: About 1.6 cm. Shape: Elliptic to ovate. Apex: Acuminate. Margin: Entire. Texture, upper surface: Smooth, glabrous. Texture, lower surface: Smooth, glabrous; ridged veins. Color, upper surface: Close to 146C. Color, lower surface: Close to 144A.

*Bracts.*—Appearance: About ten fused at base. Length: About 1.5 cm. Width: About 2 mm. Shape: Lanceolate. Apex: Acute. Margin: Entire; curved upwards. Texture, upper and lower surfaces: Smooth, glabrous. Color, upper and lower surfaces: Close to 146A to 146B.

*Peduncles.*—Length: About 3.6 cm. Diameter: About 2 mm. Angle: About 45° from vertical. Strength: Strong. Texture: Smooth, glabrous. Color: 146A.

*Reproductive organs.*—Androecium: Stamen number: Numerous, about 75. Filament length: About 2 mm. Filament color: Close to 63C. Anther shape: Bi-lobed. Anther length: About 2 mm. Anther color: Close to 10A. Amount of pollen: Moderate. Pollen color: Close to 11A. Gynoecium: Pistil length: About 5.4 cm. Style length: About 4 cm. Style color: Towards the apex, close to 54A; mid-section and towards the base, close to 155D. Stigma appearance: Flat; five-lobed. Stigma color: 53A. Ovary color: Close to 150D.

*Seed/fruit.*—Seed and fruit production has not been observed.

Low temperature tolerance: Plants of the new Hardy *Hibiscus* have been observed be hardy to USDA Zone 5.

Pathogen/pest resistance: Plants of the new Hardy *Hibiscus* have not been observed to be resistant to pathogens and pests common to Hardy *Hibiscus*.

It is claimed:

1. A new and distinct *Hibiscus* plant named 'Cherry Brandy' as illustrated and described.

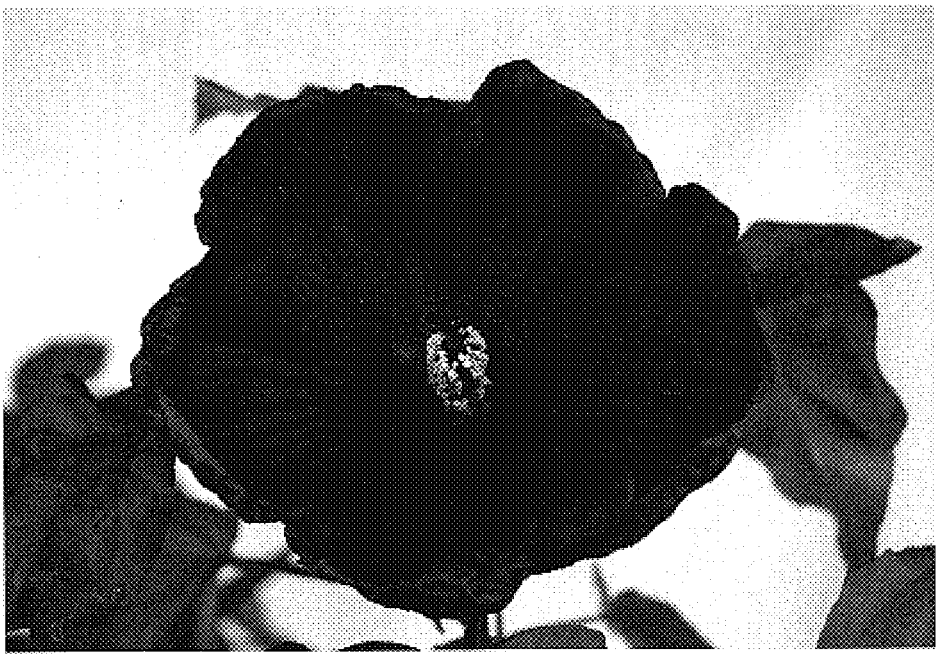
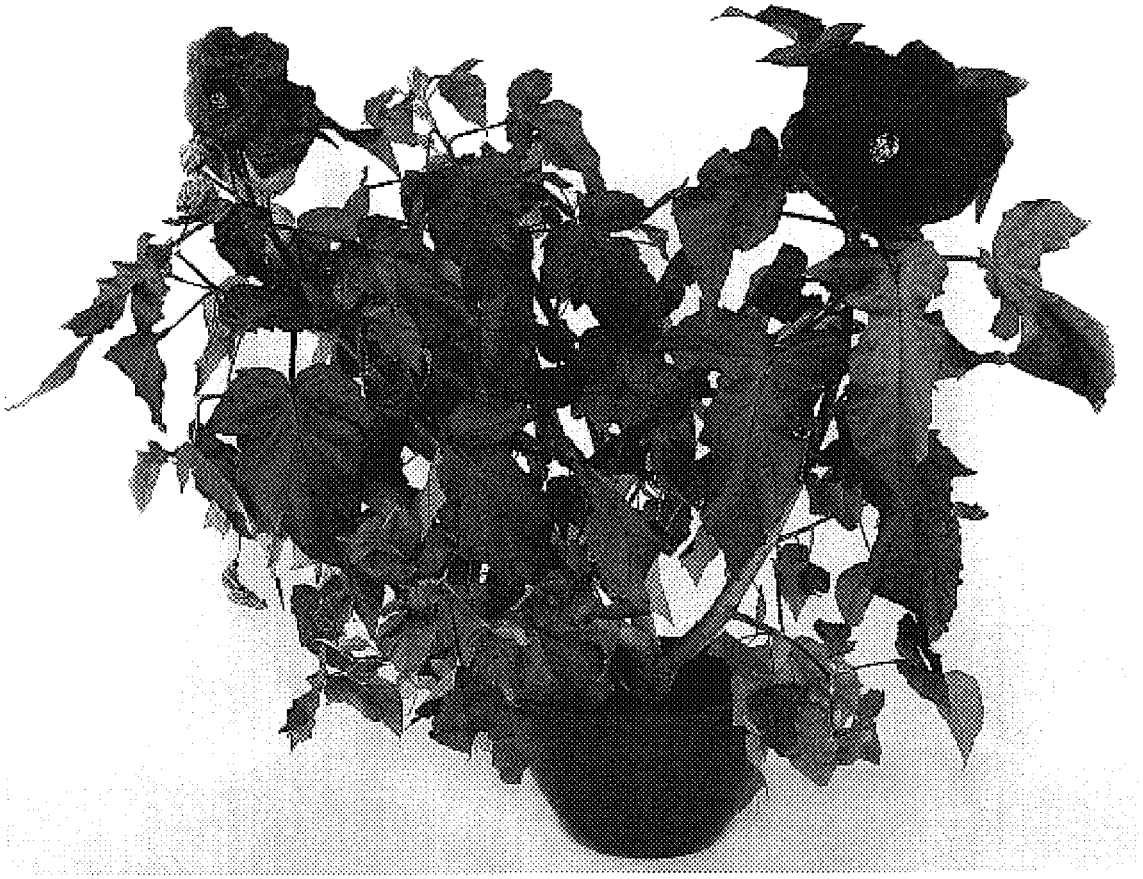

* * * * *